United States Patent [19]
Schlipalius

[11] Patent Number: 6,132,790
[45] Date of Patent: Oct. 17, 2000

[54] CAROTENOID COMPOSITION

[75] Inventor: Lance Elliott Schlipalius, Ashwood, Australia

[73] Assignee: Betatene Limited, Cheltenham, Australia

[21] Appl. No.: 08/743,174

[22] Filed: Nov. 5, 1996

Related U.S. Application Data

[62] Continuation of application No. 08/604,359, Feb. 21, 1996, abandoned, which is a continuation of application No. 08/204,188, filed as application No. PCT/AU92/00470, Sep. 7, 1992, abandoned.

[30] Foreign Application Priority Data

Sep. 6, 1991 [AU] Australia .................................. PK8258

[51] Int. Cl.$^7$ ........................................................ A23L 1/27
[52] U.S. Cl. .......................... 426/540; 426/541; 426/602; 426/250
[58] Field of Search ..................................... 426/250, 540, 426/541, 602

[56] References Cited

U.S. PATENT DOCUMENTS

| | | | |
|---|---|---|---|
| 2,861,891 | 11/1958 | Bauernfeind et al. .................. | 426/540 |
| 3,039,877 | 6/1962 | Borenstein et al. . | |
| 3,110,598 | 11/1963 | Muller et al. . | |
| 3,206,316 | 9/1965 | Klaui et al. . | |
| 3,316,101 | 4/1967 | Borenstein et al. .................... | 426/540 |
| 3,558,323 | 1/1971 | Cannalonga et al. . | |
| 3,655,406 | 4/1972 | Klaui . | |
| 3,734,745 | 5/1973 | Cassanelli et al. ..................... | 426/540 |
| 3,886,294 | 5/1975 | Emodi ..................................... | 426/540 |
| 3,998,753 | 12/1976 | Antoshkiw et al. .................... | 426/250 |
| 4,316,917 | 2/1982 | Antoshkiw et al. . | |
| 4,844,934 | 7/1989 | Leuddecke .............................. | 426/540 |
| 5,059,437 | 10/1991 | Todd ....................................... | 426/250 |
| 5,079,016 | 1/1992 | Todd ....................................... | 426/250 |
| 5,612,485 | 3/1997 | Schlipalius ............................. | 585/351 |
| 5,773,026 | 6/1998 | Schlipalius ............................. | 424/450 |

FOREIGN PATENT DOCUMENTS

| | | |
|---|---|---|
| 593081 | of 0000 | Australia . |
| 599196 | 7/1990 | Australia . |
| 3081230 | of 0000 | Japan . |
| 58001752 | of 0000 | Japan . |
| 2 248 170 | of 0000 | United Kingdom . |
| 985613 | of 0000 | United Kingdom . |
| 1363623 | 12/1974 | United Kingdom . |
| 2012547 | 1/1980 | United Kingdom . |
| 2248170 | 4/1992 | United Kingdom . |
| 9106292 | 5/1991 | WIPO . |

OTHER PUBLICATIONS

Food Manufacture, 'Facing Up to the "Additives" Challenge,' Richard Seal, vol. 61, No. 12, pp. 40–41, 1986.
R. H. Bunnell et al, "Coloring Water–Base Foods with β–Carotene," Presented at the 18th Annual Meeting of the Institute of Food Technologists, Chicago, May 25, 1958.
Howard T. Gordon et al., "Carotenoids As Food Colorants," *CRC Critical Reviews in Food Science and Nutrition*, vol. 18, Issue 1 at p. 59.
H. T. Gordon, "The Carotenoids–Current Status As Food Colorants–Current Aspects of Food Colorants," pp. 41–48.
J. N. Counsell, "Some Synthetic Carotenoids as Food Colours," *Developments in Food Colours* (Walford), Chapter 4, pp. 151–187, 1984.
Howard T. Gordon and Leonard E. Johnson, "Beta Carotene in Beverages" Presented at Society of Soft Drink Technologies, 40th Annual Conference, Fort Lauderdale, Florida, May 4, 1993.
A. Emodi, et al., "Water–Dispersible, Optically–Clear Carotenoid Colours," *Food Technology*, Jul. 1976, pp. 58–60.
J. Christopher Bauernfeind, "Carotenoids as Colorants and Vitamin A Precursors Technical and Nutritional Applications," *Food Science and Technology*, pp. 32–35, 92–99, 662–663, 790–793 (1981).
J. Paust, "Recent Progress in Commercial Retinoids and Carotenoids," *Pure & Appl. Chem.*, vol. 63, No. 1, pp. 45–58 (1991).
Neal E. Craft and Joseph H. Soares, Jr., "Relative Solubility, Stability, and Absorptivity of Lutin and β–Carotene in Organic Solvents," *Journal of Agricultural and Food Chemistry*, vol. 40, No. 3, 1992.

*Primary Examiner*—Chhaya D. Sayala
*Attorney, Agent, or Firm*—Burns, Doane, Swecker & Mathis, L.L.P.

[57] ABSTRACT

The invention is to a carotenoid composition comprising:
  a) a carotenoid in an oil solvent wherein the weight of carotenoid in the carotenoid composition is up to 12%;
  b) a dispersion of a water dispersible matrix and a stabilizer, and optionally a non-oil solvent; and
  c) an emulsifier,
wherein the carotenoid, non-oil solvent, water dispersible matrix, stabilizer and emulsifier all either exist naturally or are derived from natural sources without the use of chemical or synthesized compounds, nor chemically modified using processes of synthetic chemistry.

66 Claims, No Drawings

CAROTENOID COMPOSITION

This application is a continuation of application Ser. No. 08/604,359, filed Feb. 21, 1996, which is a continuation of application Ser. No. 08/204,188, filed Apr. 29, 1994, filed as POT/AU92/00470 filed Sep. 7, 1992, both abandoned.

FIELD OF THE INVENTION

The invention relates to a carotenoid composition derived from all natural sources, in particular, the composition is an emulsion or dried product and a process for producing an all natural carotenoid composition.

BACKGROUND OF THE INVENTION

Carotenoids are generally only soluble to any extent in lipid materials or organic solvents. Many of their applications for use, however, make it desirable that they are contained in aqueous based systems for the purposes of providing a safe source of vitamin A, colourisation (particularly food products which are generally in aqueous based materials) or as a powdered product in special preparations which are based on aqueous materials.

To overcome the virtual insolubility of carotenoids in water, so called water dispersible forms of carotenoid products are manufactured for use. They are a significant part of the economic market for carotenoids.

Recently, there has been a consumer driven preference for natural products in the market place and this has also been true for carotenoid products. The demand for products containing natural beta-carotene (a carotenoid) has grown substantially over the last five years. Natural beta-carotene is derived from certain animals, plants and microorganisms, such as the alga Dunaliella salina. However, it is inconsistent in the eyes of consumers to make a water dispersible natural carotenoid product using, for example, beta-carotene extracted from Dunaliella salina, and then to use synthetic raw materials in the manufacture of the water dispersible material. Consequently, there is a need to provide a completely natural product of water dispersible carotenoids in both a liquid emulsion and dried product form which represent the main forms in which these products are sold.

Emulsions are stable mixtures of two or more immiscible liquids held in suspension by stabilizers and small percentages of substances called emulsifiers.

Certain emulsions occur naturally. These include milk, cream, avocado, egg yolk and nuts. These emulsions contain fine dispersions of natural lipid material which are stabilized in two ways. First, by small sized droplets of fat which occur within the cell structure and cannot coalesce into larger particles due to the solidity or very high viscosity of the product. Avocado and nuts are examples of this type of emulsion. Secondly, in more fluid products with reduced viscosity, the small fat droplets are stabilized within the aqueous structure by naturally present emulsifying agents or biochemicals and by polymeric molecules of carbohydrates, proteins and lipids or combinations of all three often where the molecules are chemically bonded together which restrict the coalescing of the small lipid globules.

In more recent times these stabilizing agents have been extracted from the natural materials to provide concentrated sources of emulsifiers and stabilizers which can be used more generally for food and other biological emulsions. For example, in the preparation of salad dressing products or mayonnaise, starches, egg yolk, microbial and vegetable isolates have been selected to assist in stabilizing vegetable oils to provide a pleasing mouth texture and flavour for culinary purposes. Although the natural materials are quite satisfactory for many applications there have also been chemically modified stabilizers and emulsifiers produced which can make more stable emulsions. The chemically modified stabilizers and emulsifiers have the disadvantage that they are produced from synthetic chemical processes and for that reason they are not favoured by certain manufacturers of food products.

Previous emulsions of carotenoids have normally incorporated these chemically modified stabilizing agents for the production of carotenoid emulsions and dried water dispersible products.

It is a general requirement that carotenoids be protected against oxidation and that the liquid preparations be preserved against microbiological spoilage. For these reasons, synthetic antioxidants and synthetic preservatives have also been used in carotenoid liquid emulsions and dried powders.

The object of the invention is to provide a carotenoid composition derived principally from natural sources and a method of preparing these compositions employing a natural emulsion system to create oil in water dispersions. To achieve this result, certain mechanical and physical processes are used to provide a complete process such that a water dispersible powder and liquid emulsion product can be produced without the need for synthetic or unnatural ingredients at all.

DESCRIPTION OF THE INVENTION

According to this invention, there is provided a carotenoid composition comprising:

(a) a carotenoid in an oil solvent wherein the weight of carotenoid in the carotenoid composition is up to 12%;

(b) a dispersion of a water dispersible matrix and a stabilizer, and optionally a non-oil solvent; and (c) an emulsifier, wherein the carotenoid, non-oil solvent, water dispersible matrix, stabilizer and emulsifier all either exist naturally or are derived from natural sources without the use of chemical or synthesized compounds, nor chemically modified using processes of synthetic chemistry.

According to another form of the invention there is provided a process for producing a carotenoid composition comprising the following steps:

(a) forming an oil phase by dispersing a carotenoid in an oil solvent;

(b) forming an aqueous phase or water miscible base by dispersing a water dispersible matrix, a stabilizer and a non-oil solvent;

(c) admixing the oil phase and the aqueous phase; and (d) emulsifying the admixture with an emulsifier, wherein the carotenoid, non-oil solvent, water dispersible matrix, stabilizer and emulsifier all either exist naturally or are derived from natural sources without the use of chemical or synthesized compounds, nor chemically modified using processes of synthetic chemistry.

In a preferred form of the invention, the carotenoid composition is homogenized to help reduce the size of the oil globules in the emulsion which improves the stability and particularly helps to stop ringing of the colour at the surface of, for example, beverage products.

In a further preferred form of the invention, the carotenoid composition is dried and comprises between 0.5% to 12% by weight of carotenoid and preferably between 1% to 12% by weight of carotenoid. The dried or powdered form of the invention has particular uses in, for example, cake mixes and as drink powders and in some instances is preferred by users than the non-dried form. In this form the non-oil solvent of the emulsion is removed and the oil globules containing the carotenoid and the oil solvent are trapped in a solid continuous phase of the water dispersible matrix and stabiliser.

In the dried form, the water dispersible matrix preferably comprises up to 90% by weight and more preferably 55% to 75% of the carotenoid composition.

In three preferred forms of the invention, when the carotenoid composition is an emulsion, the emulsion comprises up to 7.5%, between 0.1% and 6% and between 2% and 5% by weight of carotenoid. Preferably, the carotenoid is selected from fat soluble retinoids, beta-carotene, lutein, lycopene, astaxanthin, canthaxanthin, phytoene, alpha-carotene, apo carotenal, retinol, capsanthin, oleo resin paprika, zeaxanthin, beta-cryptoxanthin, phytofluene, gamma-carotene and natural carotenoid isolates and mixtures thereof.

In another form of the invention the water dispersible matrix is comprised of a non-oil solvent and any of a non-oil solvent soluble matrix and a non-oil solvent soluble anti-oxidant. In the preferred forms of the invention the solvent soluble matrix is a combination of any one or more of sucrose, glucose, fructose, mannose, pentoses, maltose and malto dextrins, the non-oil solvent is selected from water, glycerol and mixtures thereof and the non-oil solvent soluble anti-oxidant is a combination of any one or more of natural ascorbic acid from rosehip or acerola.

In yet another preferred form of the invention, the oil solvent contains an oil soluble antioxidant that either exists naturally or is derived from natural sources without the use of chemical or synthesized compounds, nor chemically modified using processes of synthetic chemistry. The oil soluble anti-oxidant comprises 0.1% to 2% and more preferably 0.2% to 1% by weight of the carotenoid composition. Typically the anti-oxidant is a combination of natural mixed tocopherols and other plant extracts having anti-oxidant activity. More preferably, the plant extract is selected from rosemary, eucalyptus and olive.

Preferably the oil solvent is selected from animal, vegetable or mineral oils including but not limited to soyabean, peanut, lard, olive, corn, coconut, fish, terpenoid and essential oils. Preferably these oils should be cold pressed.

The emulsifier preferably comprises 0.01% to 3% and more preferably 0.03% to 1% by weight of the carotenoid composition and is selected from extracts of animals and plants, phospholipid extracts of natural products, saponins, lecithins, milk isolates and egg products including egg yolks.

Preferably the invention further comprises a stabilizer which comprises 1% to 30% and preferably 5% to 25% by weight of the carotenoid composition. Typically the stabilizer is selected from hydrocolloids derived from natural plant and animal sources; guar, xanthan, carob, karaya, arabic, acacia and furcellaran gums; and carrageenans, alginates, celluloses, gelatins, starches, amylose, amylopectin, caseins and caseinates.

In yet a further preferred embodiment of the invention the carotenoid composition further comprises an acidulant to assist microbiological stability. The acidulant either exists naturally or is derived from natural sources without the use of chemical or synthesized compounds, nor chemically modified using processes of synthetic chemistry. Typically these are selected from naturally derived acids including citric, tartaric, ascorbic, maleic, lactic and fruit juices and other vegetable sources containing acids. The acidulant is added to the aqueous phase to adjust the pH of the aqueous phase to within the range of 2 to 5.5 and more preferably within the range 3.5 to 4.0 which assists the microbiological stability of the composition.

Preferably the carotenoid, oil solvent, water dispersible matrix, stabilizer, emulsifier, anti-oxidants and acidulant in the process for producing a carotenoid composition are also included in the groups outlined above.

In a further preferred form of the invention the process for producing a carotenoid composition includes the step of homogenizing the emulsion to obtain a fine particle structure preferably within the range 0.01 and 10 microns and more preferably within the range 0.1 to 2.0 microns. Homogenization helps to reduce the size of the oil globules in the emulsion which improves its stability and in particular helps to stop ringing of the colour at the surface of, for example, beverage products.

Preferably, the process further comprises the step of heating the admixture of the oil phase the aqueous phase prior to emulsification to a temperature of between 60° C. and 150° C. and holding the admixture at this temperature for sufficient time to assist the microbiological control of the product (for longer term storage). Thereafter, emulsification may take place. Typically, the material is then packed, and preferably aseptically filled into containers.

In yet a further form of the invention, the process includes the step of drying the emulsion to form a powder and preferably, the emulsion is dried using a spray drier. The dried form has particular preferred uses as described above.

In another form of the invention a carotenoid composition is provided when produced by the invention processes.

In yet a final preferred form of the invention a process to produce a composition is provided which comprises the steps of:

(a) forming an oil phase by dispersing the carotenoid in the oil solvent;

(b) forming an aqueous phase by dispersing the water dispersible matrix, the stabilizer and the non-oil solvent;

(c) admixing the oil phase and the aqueous phase; and (d) emulsifying the admixture with the emulsifier.

References in this specification to a particular group of components is a reference both to each individual component and to any combination of those components.

As indicated above, this invention uses only natural materials as the source of carotenoids, emulsifiers, solvent soluble matrices, stabilizers, anti-oxidants, acidulants and solvents and uses a physical technique for microbiological preservation rather than a chemical technique.

ILLUSTRATIONS OF THE INVENTION

The invention is illustrated by the following non-limiting examples.

EXAMPLE 1

An aqueous dispersion of sucrose, gum acacia, citric acid, egg yolk powder and acerola powder is created in water. A dispersion of the oil based mixture containing the solubilized carotenoid in soya bean oil is mixed with natural tocopherols as the anti-oxidant and is dispersed into the aqueous phase. The material is finely emulsified at temperatures between 50° and 80° C., subsequently homogenized to obtain a fine particle structure of between 0.01 and 10.0 microns and preferably between 0.1 and 2.0 microns. This emulsion is then held at a temperature of 75° C. for sufficient time to render the microbiological load satisfactory for longer term storage. The material is then packed into suitable containers which are hermetically sealed. The product in the container is then cooled to ambient temperature.

EXAMPLE 2

The same procedure and conditions in example 1 and further, the emulsion is dried on a spray drier to form a microencapsulated or similar finished product which as a powder is stable to oxidation and microbiological spoilage and is packaged in a suitable reduced oxygen permeability package to maintain stability of the carotenoid over a period of time of about six to twelve months.

EXAMPLE 3

A typical emulsion and dried product composition is:

|  | Emulsion | | Dried Product |
| --- | --- | --- | --- |
|  | Wt gms | % w/w | % w/w |
| Sugar (matrix) | 360 | 18.0 | 33.4 |
| Gum acacia (stabilizer) | 360 | 18.0 | 33.4 |
| Egg yolk powder (emulsifier) | 5 | 0.25 | 0.47 |
| Acerola powder (anti-oxidant) | 10 | 0.5 | 0.93 |
| Citric acid (acidulent) | 5 | 0.25 | 0.46 |
| Mixed tocopherols (anti-oxidant) | 8 | 0.4 | 0.74 |
| Natural betacarotene (carotenoid) | 75 | 3.75 | 6.96 |
| Oil | 175 | 8.75 | 16.24 |
| Water | 1002 | 50.1 | 7.4 |
|  | 2000 g | 100 | 100 |

The dried product is the emulsion with approximately 92% of the water removed.

The composition of the invention is naturally derived as specified above and therefore is more acceptable as a food additive. Its preparation involves the formation of the carotenoid in an oil phase using a natural oil solvent, the dispersion of this into the aqueous phase of water dispersible matrix and stabilizer followed by emulsification. This emulsion can then be optionally spray dried to form a dried powder.

I claim:

1. A stable carotenoid composition comprising:
   a) a carotenoid in an oil solvent wherein the weight of carotenoid in the carotenoid composition is up to 12%;
   b) a dispersion of a water dispersible matrix and a stabilizer, and optionally a non-oil solvent; and
   c) an emulsifier,
wherein the carotenoid, non-oil solvent, water-dispersible matrix, stabilizer and emulsifier all are in the form in which they exist naturally or are derived from natural sources without the use of synthetic compounds, and further wherein the carotenoid, non-oil solvent, water-dispersible matrix, stabilizer, and emulsifier are not chemically modified using processes of synthetic chemistry.

2. A carotenoid composition according to claim 1 wherein the composition is homogeneous.

3. A carotenoid composition according to either claims 1 or 2 wherein the composition is dried and comprises between 0.5% to 12% by weight of carotenoid.

4. A carotenoid composition according to claim 3 wherein the composition comprises between 1% to 12% by weight of carotenoid.

5. A carotenoid composition according to either claims 1 or 2 wherein the composition is dried and the water dispersible matrix and stabilizer comprises up to 90% by weight of the carotenoid composition.

6. A carotenoid composition according to claim 5 wherein the matrix comprises 55% to 75% by weight of the carotenoid composition.

7. A carotenoid composition according to claim 1 wherein the emulsion comprises up to 7.5% by weight of carotenoid.

8. A carotenoid composition according to claim 1 wherein the emulsion comprises between 0.1% and 6% by weight of carotenoid.

9. A carotenoid composition according to claim 1 wherein the emulsion comprises between 2% and 5% by weight of carotenoid.

10. A carotenoid composition according to claim 1 wherein the carotenoid is selected from fat soluble retinoids, beta-carotene, lutein, lycopene, astaxanthin, canthaxanthin, phytoene, alpha-carotene, apo-carotenal, retinol, capsanthin, oleo resin paprika, zeaxanthin, beta-cryptoxanthin, phytofluene, gamma-carotene, natural carotenoid isolates, sources and mixtures thereof.

11. A carotenoid composition according to claim 1 wherein the matrix comprises a non-oil solvent and either a non-oil solvent soluble matrix or a non-oil solvent soluble anti-oxidant.

12. A carotenoid composition according to claim 11 wherein the non-oil solvent soluble matrix is a combination of any one or more of sucrose, glucose, fructose, mannose, pentoses, maltose and malto dextrins.

13. A carotenoid composition according to claim 11 wherein the non-oil solvent is selected from water, glycerol and mixtures thereof.

14. A carotenoid composition according to claim 11 wherein the non-oil solvent soluble antioxidant comprises natural ascorbic acid derived from rosehip or acerola.

15. A carotenoid composition according to claim 1 wherein the oil solvent contains an oil soluble anti-oxidant that either exists naturally or is derived from natural sources without the use of chemical or synthesized compounds, nor chemically modified using processes of synthetic chemistry and comprises 0.1% to 2% by weight of the carotenoid composition.

16. A carotenoid composition according to claim 15 wherein the oil soluble anti-oxidant comprises 0.2% to 1% by weight of the carotenoid composition.

17. A carotenoid composition according to claim 15 wherein the oil soluble anti-oxidant is a combination of plant extracts having anti-oxidant activity comprising natural mixed tocopherols.

18. A carotenoid composition according to claim 17 wherein the plant extracts are selected from rosemary, eucalyptus and olive.

19. A carotenoid composition according to claim 1 wherein the oil solvent is selected from soyabean, peanut, lard, olive, corn, coconut, fish, terpenoid and essential oil.

20. A carotenoid composition according to claim 1 wherein the emulsifier comprises 0.01% to 3% by weight of the carotenoid composition.

21. A carotenoid composition according to claim 1 wherein the emulsifier comprises 0.03% to 1% by weight of the carotenoid composition.

22. A carotenoid composition according to claim 1 wherein the emulsifier is selected from the group consisting of animal extracts, plant extracts, phospholipids, saponins, lecithins, milk isolates and egg products.

23. A carotenoid composition according to claim 1 wherein the stabilizer comprises 1% to 30% by weight of the carotenoid composition.

24. A carotenoid composition according to claim 23 wherein the stabilizer comprises 5% to 25% by weight of the carotenoid composition.

25. A carotenoid composition according to claim 1 wherein the stabilizer is selected from hydrocolloids derived from natural plant and animal sources; guar, xanthan, carob, karaya, arabic, acacia and fucellaran gums; carrageenans, alginates, celluloses, gelatins, starches, amylose, amylopectin, caseins and caseinates.

26. A carotenoid composition according to claim 1 further comprising an acidulant that is in the form in which it exists naturally or is derived from natural sources without the use of synthetic compounds, and further wherein the acidulant is not chemically modified using processes of synthetic chemistry.

27. A carotenoid composition according to claim 26 wherein the acidulant is selected from naturally derived acids including citric acid, tartaric acid, ascorbic acid, maleic acid, lactic acid, fruit juices, and acidic plant materials.

28. A process for producing a stable carotenoid composition comprising the following steps:
   (a) forming an oil phase by dispersing a carotenoid in an oil solvent;
   (b) forming an aqueous phase by dispersing a water dispersible matrix, a stabilizer and non-oil solvent;
   (c) admixing the oil phase and the aqueous phase; and
   (d) emulsifying the admixture with an emulsifier,
wherein the carotenoid, non-oil solvent, water-dispersible matrix, stabilizer and emulsifier all are in the form in which they exist naturally or are derived from natural sources without the use of synthetic compounds, and further wherein the carotenoid, non-oil solvent, water-dispersible matrix, stabilizer, and emulsifier are not chemically modified using processes of synthetic chemistry.

29. The process for producing a carotenoid composition according to claim 28 wherein the carotenoid is selected from fat soluble retinoids, beta-carotene, lutein, lycopene, astaxanthin, canthaxanthin, phytoene, alpha-carotene, apo carotenal, retinol, capsanthin, zeaxanthin, beta-cryptoxanthin, phytofluene, gamma-carotene and natural carotenoid isolates and mixtures thereof.

30. The process for producing a carotenoid composition according to claim 28 wherein the oil solvent is selected from soyabean, peanut, lard, olive, corn, coconut, fish, terpenoid and essential oils.

31. The process for producing a carotenoid composition according to claim 28 wherein the matrix is comprised of a non-oil solvent and any one of a non-oil solvent soluble matrix and a non-oil solvent soluble anti-oxidant.

32. The process for producing a carotenoid composition according to claim 31 wherein the non-oil solvent soluble matrix comprises one or more carbohydrates selected from the group consisting of sucrose, glucose, fructose, mannose, pentoses, maltose and, malto dextrins.

33. The process for producing a carotenoid composition according to claim 31 wherein the non-oil solvent is selected from water, glycerol and mixtures thereof.

34. The process for producing a carotenoid composition according to claim 31 wherein the non-oil solvent soluble anti-oxidant comprises natural ascorbic acid derived from rosehip or acerola.

35. The process for producing a carotenoid composition according to claim 28 wherein the oil solvent contains an oil soluble anti-oxidant which comprises a combination of plant extracts having anti-oxidant activity comprising natural mixed tocopherols.

36. The process for producing a carotenoid composition according to claim 35 wherein the plant extract is selected from rosemary, eucalyptus and olive.

37. The process for producing a carotenoid composition according to claim 28 wherein the stabilizer is selected from hydrocolloids derived from natural plant and animal sources; guar, xanthan, carob, karaya, arabic, acacia and fucellaran gums; carrageenans, alginates, celluloses, gelatins, starches, amylose, amylopectin, caseins and caseinates.

38. The process for producing a carotenoid composition according to claim 28 wherein the emulsifier is selected from the group consisting of animal extracts, plant extracts, phospholipids, saponins, lecithins, milk isolates and egg products.

39. The process for producing a carotenoid composition according to any one of claims 28 to 38 further comprising after step (d), the step of homogenizing the emulsion to obtain a fine particle structure.

40. The process for producing a carotenoid composition according to claim 39 wherein the fine particle structure is within 0.01 and 10 microns.

41. The process for producing a carotenoid composition according to claim 39 wherein the fine particle structure is within 0.1 to 2.0 microns.

42. The process for producing a carotenoid composition according to claim 28 further comprising the step of adding an acidulant to the aqueous phase to adjust the pH of the aqueous phase to within the range of 2 to 5.5.

43. The process for producing a carotenoid composition according to claim 28 further comprising the step of adding an acidulant to the aqueous phase to adjust the pH of the aqueous phase to within the range of 3.5 to 4.0, wherein the acidulant is in the form in which it exists naturally or is derived from natural sources without the use of synthetic compounds, and further wherein the acidulant is not chemically modified using processes of synthetic chemistry.

44. The process for producing a carotenoid composition according to claim 28 further comprising between step (c) and step (d), the step of heating the admixture to a temperature of between 60° C. and 150° C.

45. The process for producing a carotenoid composition according to claim 28 further comprising the step of drying the emulsion to form a powder.

46. The process for producing a carotenoid composition according to claim 45 wherein the emulsion is dried using a spray drier.

47. A carotenoid composition produced by the process as claimed in claim 28.

48. A process to produce a composition according to claim 1 comprising the steps of:
   (a) forming an oil phase by dispersing the carotenoid in the oil solvent;
   (b) forming an aqueous phase by dispersing the water dispersible matrix, the stabilizer and the non-oil solvent;
   (c) admixing the oil phase and the aqueous phase; and
   (d) emulsifying the admixture with the emulsifier.

49. A stable carotenoid composition comprising
   (a) a carotenoid in an oil solvent wherein the weight of carotenoid in the carotenoid composition is up to 12%;
   (b) a dispersion of
      a water dispersible matrix and
      a stabilizer,
      wherein the water dispersible matrix comprises:
         a non-oil solvent a non-oil solvent soluble matrix and a non-oil solvent soluble anti-oxidant; and (c) an emulsifier, wherein the carotenoid, water dispersible matrix, stabilizer, and emulsifier are derived from natural sources.

50. A carotenoid composition according to claim 49, wherein the non-oil solvent is optionally removed to form a dry and/or powdered carotenoid composition.

51. A carotenoid composition according to claim 50, wherein the composition comprises between 0.5% to 12% by weight of carotenoid.

52. A carotenoid composition according to claim 50, wherein the water dispersible matrix and stabilizer comprises up to 90% by weight of the carotenoid composition.

53. A stable carotenoid composition comprising:

(a) a carotenoid in oil solvent where the weight of the carotenoid in the carotenoid composition is up to 12%;

(b) a dispersion of a water dispersible matrix and a stabilizer; and (c) an emulsifier, wherein the carotenoid, water-dispersible matrix, stabilizer, non-oil solvent and emulsifier are derived from natural sources, and wherein the emulsifier used to form the composition is in a naturally-occurring matrix.

54. A carotenoid composition according to claim 53, wherein the dispersion further comprises a non-oil solvent.

55. A carotenoid composition according to claim 53, wherein the composition is dried and comprises 0.5% to 12% by weight of the carotenoid.

56. A carotenoid composition according to claim 53, wherein the composition is dried and the water dispersible matrix and stabilizer comprises up to 90% by weight of the carotenoid composition.

57. A process for producing a stable carotenoid composition comprising the following steps:

(a) forming an oil phase by dispersing a carotenoid in an oil solvent;

(b) forming an aqueous phase by dispersing a water dispersible matrix and a stabilizer, wherein the water dispersible matrix comprises:

a non-oil solvent a non-oil solvent soluble matrix and a non-oil solvent soluble anti-oxidant;

(c) admixing the oil phase and the aqueous phase; and (d) emulsifying the admixture with an emulsifier, wherein the carotenoid, water dispersible matrix, stabilizer, and emulsifier are derived from natural sources.

58. A process according to claim 57, further comprising the step of drying the emulsion to form a powder.

59. A process for producing a stable carotenoid composition comprising the following steps:

(a) forming an oil phase by dispersing a carotenoid in an oil solvent;

(b) forming an aqueous phase by dispersing a water dispersible matrix, a non-oil solvent and a stabilizer;

(c) admixing the oil phase and the aqueous phase; and (d) emulsifying the admixture with an emulsifier, wherein the carotenoid, water dispersible matrix, stabilizer and emulsifier are derived from natural sources, and wherein the emulsifier used to form the composition is in a naturally occurring matrix.

60. A process according to claim 59, further comprising the step of drying the emulsion to form a powder.

61. A stable carotenoid composition comprising:

(a) a carotenoid in an oil solvent wherein the weight of carotenoid in the carotenoid composition is up to 12%;

(b) a dispersion of a water soluble matrix, and a stabilizer, the dispersion having a pH within the range of 2.0 to 5.5; and (c) an emulsifier;

wherein the carotenoid, water dispersible matrix, stabilizer and emulsifier are derived from natural sources.

62. A carotenoid composition according to claim 61, wherein the dispersion further comprises a non-oil solvent.

63. A carotenoid composition according to claim 61 wherein the composition is dried and comprises 0.5% to 12% by weight of carotenoid.

64. A carotenoid composition according to claim 61, wherein the composition is dried and the water dispersible matrix and stabilizer comprises up to 90% by weight of the carotenoid composition.

65. A process for producing a stable carotenoid composition comprising the following steps:

(a) forming an oil phase by dispersing a carotenoid in an oil solvent;

(b) forming an aqueous phase by dispersing a water soluble matrix, a non-oil solvent and a stabilizer, wherein the pH of the aqueous phase is adjusted by adding an acidulant such that the pH of said phase is in the range of 2.0 to 5.5;

(c) admixing the oil phase and the aqueous phase; and (d) emulsifying the admixture with an emulsifier, wherein the carotenoid, non-oil solvent, water dispersible matrix, stabilizer, acidulant and emulsifier are derived from natural sources.

66. A process according to claim 65, further comprising the step of drying the emulsion to form a powder.

* * * * *